US010589025B2

(12) United States Patent
McLaughlin

(10) Patent No.: US 10,589,025 B2
(45) Date of Patent: *Mar. 17, 2020

(54) DRUG DELIVERY SYSTEMS WITH SEALED AND STERILE FLUID PATHS AND METHODS OF PROVIDING THE SAME

(71) Applicant: Insulet Corporation, Acton, MA (US)

(72) Inventor: Ian McLaughlin, Groton, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,996

(22) Filed: Feb. 19, 2019

(65) Prior Publication Data

US 2019/0175832 A1 Jun. 13, 2019

Related U.S. Application Data

(63) Continuation of application No. 15/809,532, filed on Nov. 10, 2017, now Pat. No. 10,245,377.

(60) Provisional application No. 62/422,291, filed on Nov. 15, 2016, provisional application No. 62/421,648, filed on Nov. 14, 2016, provisional application No. 62/420,736, filed on Nov. 11, 2016.

(51) Int. Cl.
| | |
|---|---|
| *A61M 5/19* | (2006.01) |
| *A61M 5/168* | (2006.01) |
| *A61M 5/24* | (2006.01) |
| *A61L 2/00* | (2006.01) |
| *A61L 2/08* | (2006.01) |

(Continued)

(52) U.S. Cl.
CPC ........... *A61M 5/16827* (2013.01); *A61L 2/00* (2013.01); *A61L 2/087* (2013.01); *A61M 5/162* (2013.01); *A61M 5/2466* (2013.01); *A61L 2/07* (2013.01); *A61L 2/081* (2013.01); *A61L 2/082* (2013.01); *A61L 2/206* (2013.01); *A61L 2202/23* (2013.01); *A61M 5/001* (2013.01); *A61M 5/14566* (2013.01); *A61M 5/19* (2013.01); *A61M 2005/3118* (2013.01); *A61M 2005/3132* (2013.01); *A61M 2005/3258* (2013.01); *A61M 2039/1072* (2013.01)

(58) Field of Classification Search
USPC .......................................... 604/151
See application file for complete search history.

(56) References Cited

U.S. PATENT DOCUMENTS

| | | | |
|---|---|---|---|
| 4,850,954 A | 7/1989 | Charvin | |
| 5,899,882 A * | 5/1999 | Waksman | A61M 25/1002 604/103.07 |

(Continued)

FOREIGN PATENT DOCUMENTS

| | | |
|---|---|---|
| EP | 2099384 A1 | 9/2009 |
| ES | 2559866 T3 | 2/2016 |

(Continued)

OTHER PUBLICATIONS

International Search Report and Written Opinion for Application No. PCT/US18/52468, dated Feb. 26, 2019, 18 pages.

*Primary Examiner* — Phillip A Johnston

(57) ABSTRACT

The present disclosure relates generally to the field of drug delivery. In particular, the present disclosure relates to a drug delivery system that includes a sealed and sterile fluid path attached to a drug-loaded container. The disclosure further relates to methods for sterilizing a portion of the drug delivery system without exposing the drug-loaded container to harmful sterilization parameters.

12 Claims, 11 Drawing Sheets

(51) Int. Cl.
  *A61M 5/162*  (2006.01)
  *A61M 5/31*   (2006.01)
  *A61M 5/32*   (2006.01)
  *A61M 39/10*  (2006.01)
  *A61L 2/07*   (2006.01)
  *A61L 2/20*   (2006.01)
  *A61M 5/00*   (2006.01)
  *A61M 5/145*  (2006.01)

(56) References Cited

U.S. PATENT DOCUMENTS

| | | | |
|---|---|---|---|
| 7,303,073 B2 | 12/2007 | Raynal-Olive et al. | |
| 8,056,719 B2 | 11/2011 | Porret et al. | |
| 8,105,282 B2* | 1/2012 | Susi | A61M 5/14228 |
| | | | 604/151 |
| 8,461,561 B2* | 6/2013 | Freeman | A61L 2/081 |
| | | | 250/505.1 |
| 8,727,117 B2 | 5/2014 | Maasarani | |
| 9,248,229 B2 | 2/2016 | Devouassoux et al. | |
| 9,427,710 B2 | 8/2016 | Jansen | |
| 9,555,911 B2 | 1/2017 | Pawlowski et al. | |
| 9,598,195 B2 | 3/2017 | Deutschle et al. | |
| 9,862,519 B2 | 1/2018 | Deutschle et al. | |
| 10,086,131 B2 | 10/2018 | Okihara | |
| 10,342,926 B2 | 7/2019 | Nazzaro et al. | |
| 2014/0163664 A1* | 6/2014 | Goldsmith | A61B 17/00491 |
| | | | 623/1.11 |

FOREIGN PATENT DOCUMENTS

| | | | |
|---|---|---|---|
| WO | 2017089289 A1 | 6/2017 | |
| WO | 2017205816 A1 | 11/2017 | |

\* cited by examiner

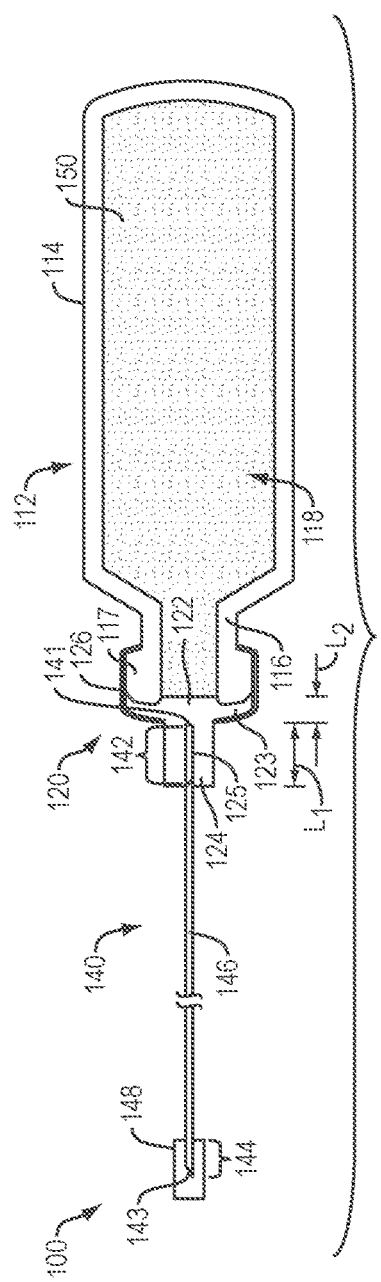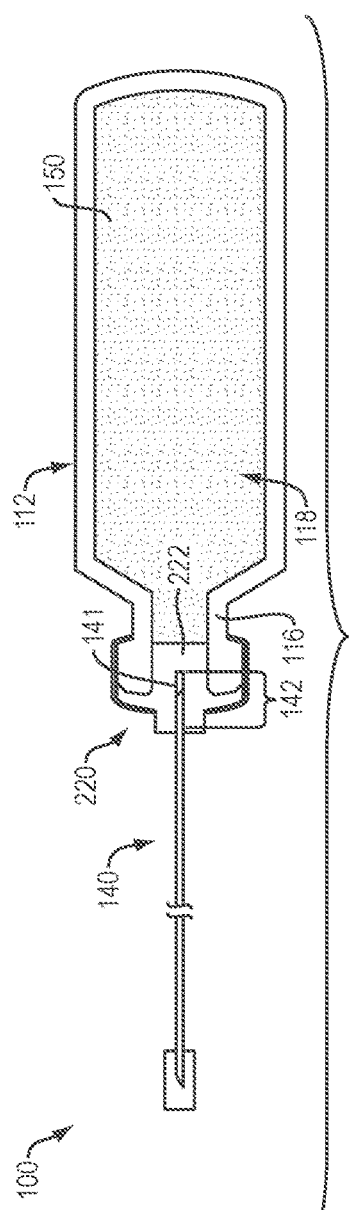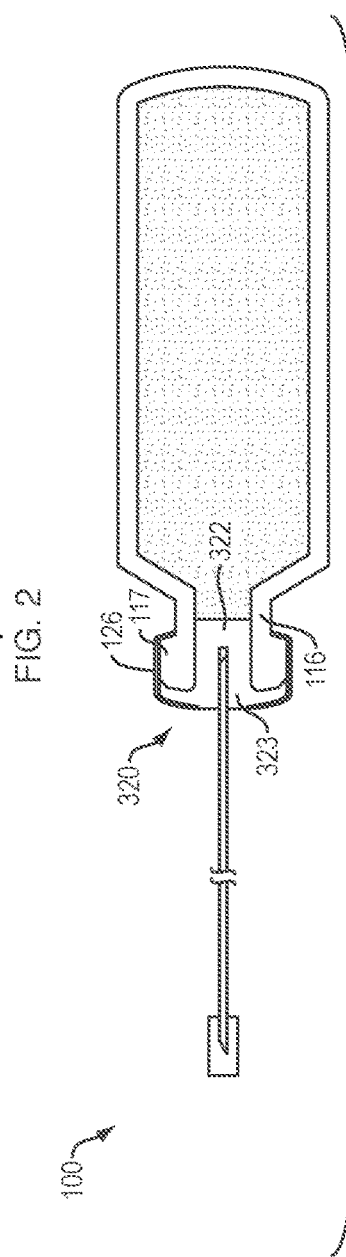

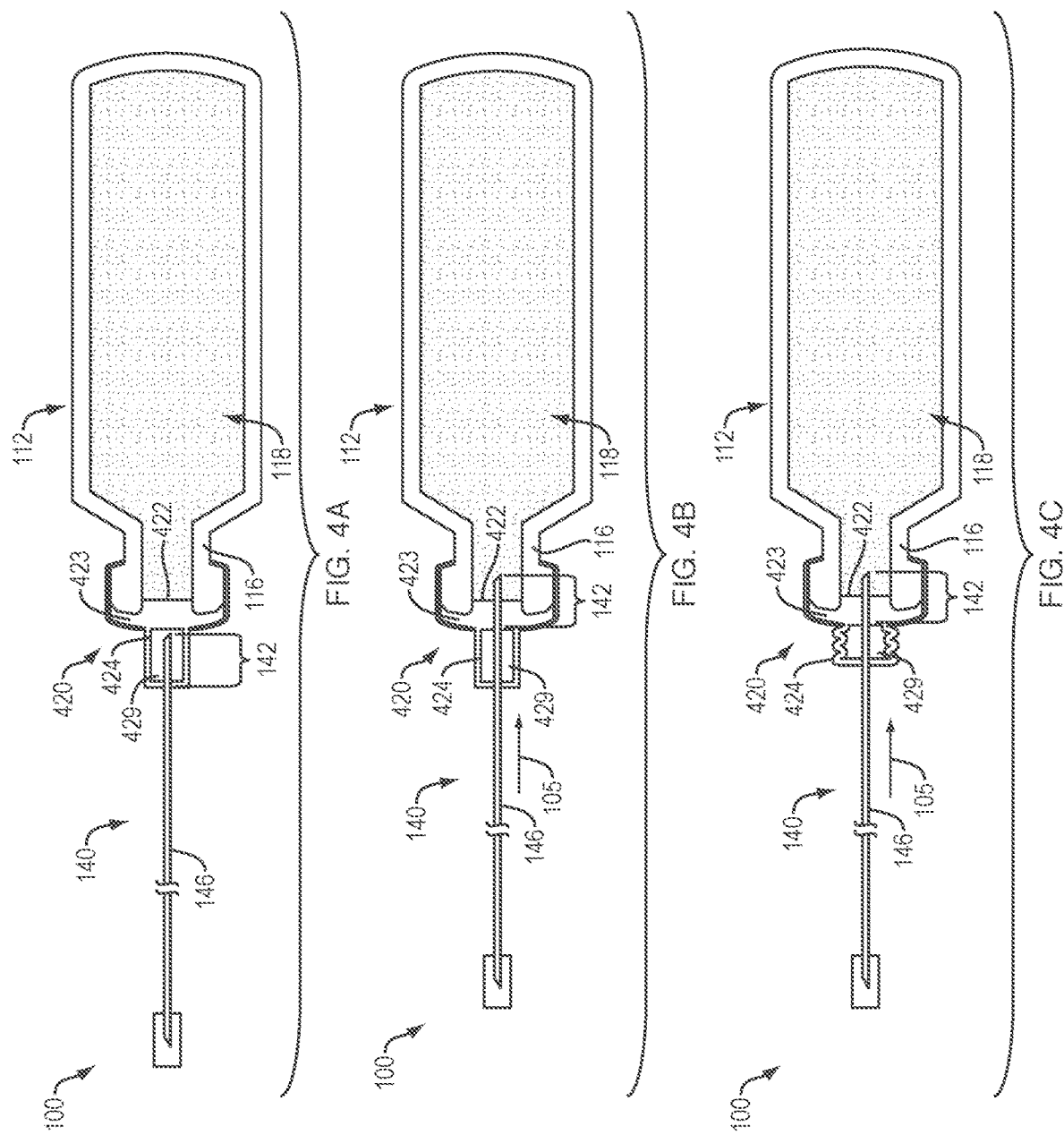

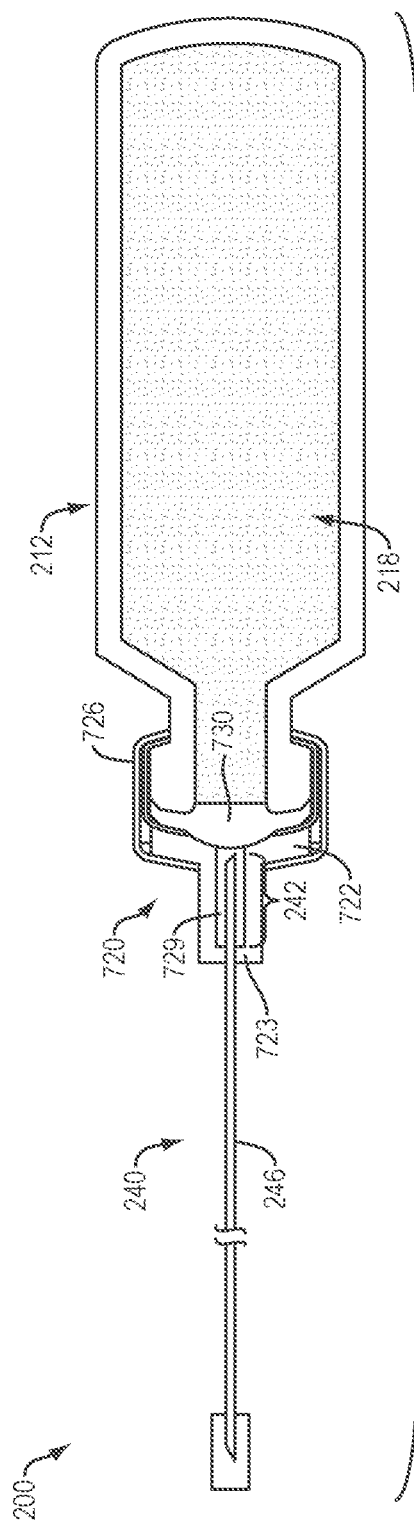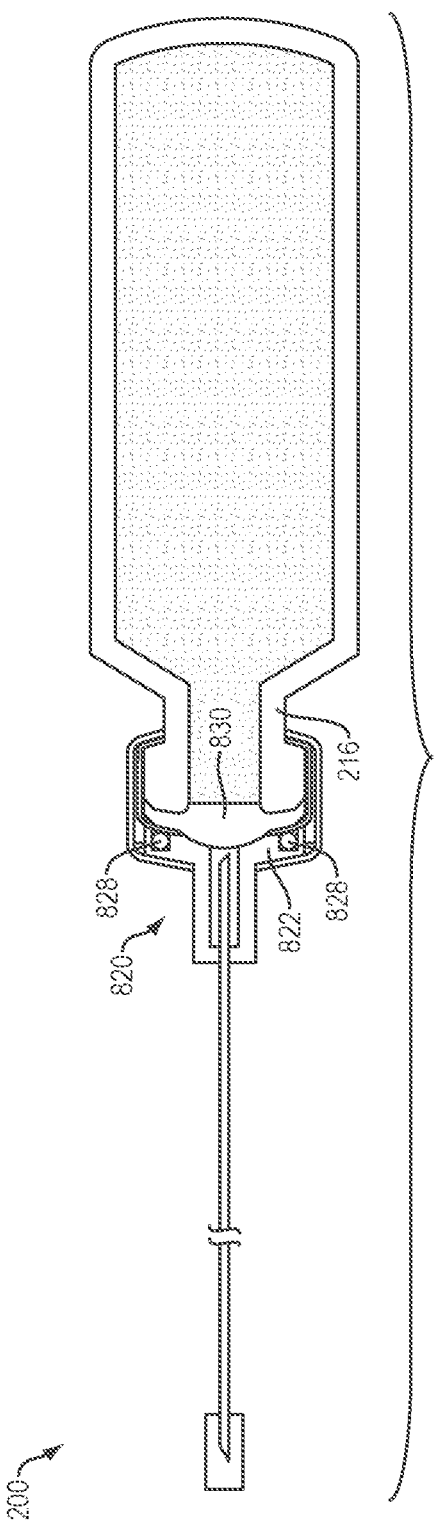

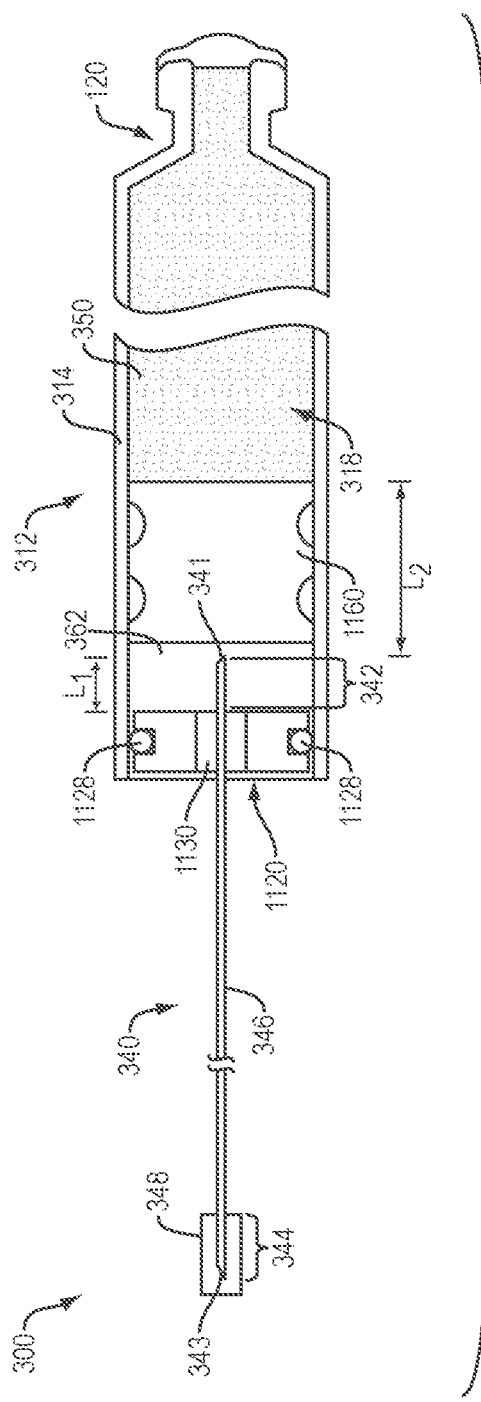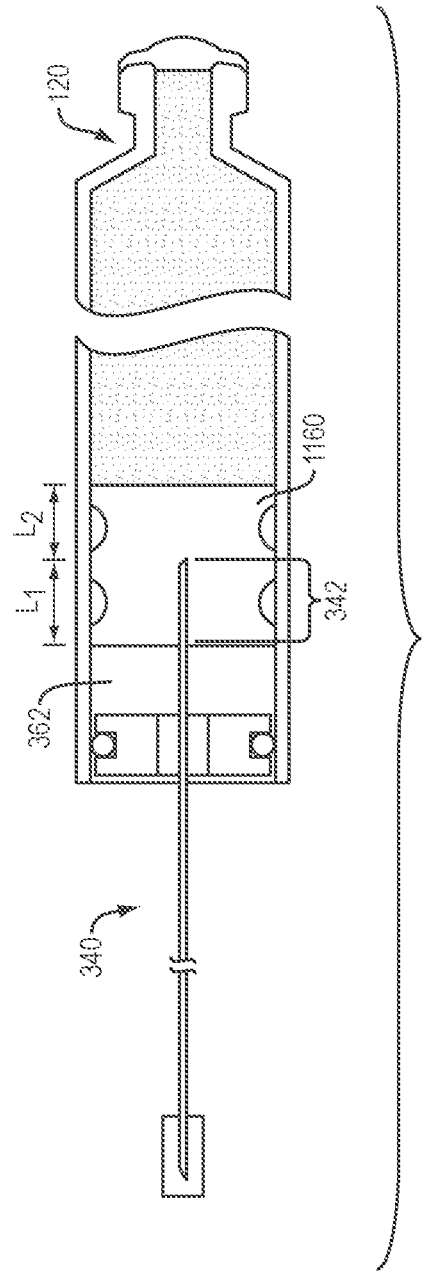

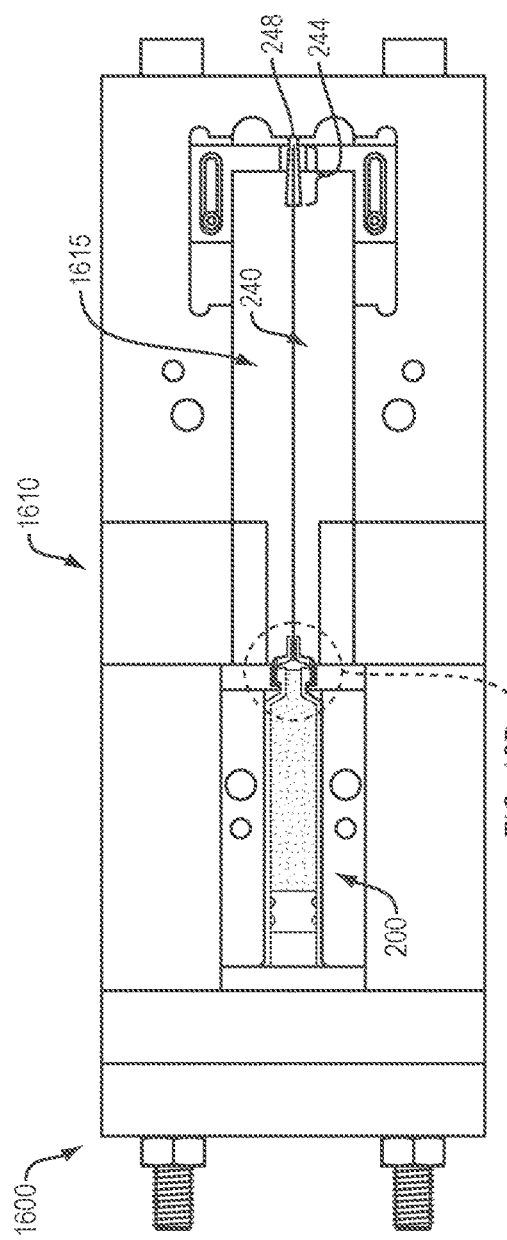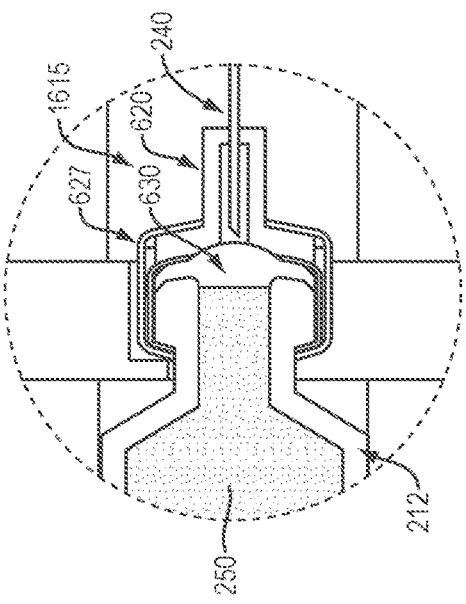

DRUG DELIVERY SYSTEMS WITH SEALED AND STERILE FLUID PATHS AND METHODS OF PROVIDING THE SAME

CROSS-REFERENCE TO RELATED APPLICATIONS

This application is a continuation of U.S. patent application Ser. No. 15/809,532, entitled "DRUG DELIVERY SYSTEMS WITH SEALED AND STERILE FLUID PATHS AND METHODS OF PROVIDING THE SAME", filed Nov. 10, 2017 which claims the benefit of U.S. Provisional Application No. 62/420,736, filed Nov. 11, 2016, U.S. Provisional Application No. 62/421,648, filed Nov. 14, 2016 and U.S. Provisional Application No. 62/422,291, filed Nov. 15, 2016, the disclosures of which are incorporated herein by reference in their entirety.

TECHNICAL FIELD

The present disclosure relates generally to the field of drug delivery. In particular, the present disclosure relates to drug delivery systems that include a sealed and sterile fluid path attached to a drug-loaded container. The disclosure further relates to methods for sterilizing the drug delivery systems without exposing the drug-loaded container to harmful sterilization parameters.

BACKGROUND

Conventional drug delivery systems are not optimized for post-assembly sterilization protocols because the sterilization modality (e.g., heat, pressure, radiation, etc.) can tend to degrade or destroy the drug(s) contained within such systems. The inability to provide a sealed and sterile fluid path attached to a drug-loaded container requires that conventional drug delivery systems provide the fluid path and drug-loaded container as separate components. A user is thus required to assemble these components into a combined device prior to drug administration. In addition to the increased costs associated with individually packaging and shipping these components, the time required to assemble the drug delivery system may result in significant inconvenience to the user. For example, the time required for an individual experiencing a severe allergic reaction to assemble a drug delivery system (e.g., epinephrine pens, etc.) may be the difference between life and death. Similarly, the time required for medical personnel to load an empty syringe with the proper type and dosage of drug may unnecessarily prolong the administration of the drug during an emergency situation.

A variety of advantageous medical outcomes may be realized by the systems and/or methods of the present disclosure, which provide a drug delivery system that includes a sealed and sterile fluid path attached to a drug-loaded container.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 provides a schematic view of a single-barrier drug delivery system, according to one embodiment of the present disclosure.

FIG. 2 provides a schematic view of an alternative single-barrier drug delivery system, according to one embodiment of the present disclosure.

FIG. 3 provides a schematic view of an alternative single-barrier drug delivery system, according to one embodiment of the present disclosure.

FIG. 4A provides a first schematic view of an alternative single-barrier drug delivery system, according to one embodiment of the present disclosure.

FIG. 4B provides a second schematic view of an alternative single-barrier drug delivery system, according to one embodiment of the present disclosure.

FIG. 4C provides a third schematic view of an alternative single-barrier drug delivery system, according to one embodiment of the present disclosure.

FIG. 7 provides a schematic view of an alternative double-barrier drug delivery system, according to one embodiment of the present disclosure.

FIG. 8 provides a schematic view of an alternative double-barrier drug delivery system, according to one embodiment of the present disclosure.

FIG. 11 provides a schematic view of a plunger drug delivery system, according to one embodiment of the present disclosure.

FIG. 12 provides a schematic view of an alternative plunger drug delivery system, according to one embodiment of the present disclosure.

FIG. 16A provides a first schematic view of a double-barrier drug delivery system disposed within a shield assembly, according to one embodiment of the present disclosure.

FIG. 16B provides a second schematic view of a double-barrier drug delivery system disposed within a shield assembly, according to one embodiment of the present disclosure.

DETAILED DESCRIPTION

Figure 5:
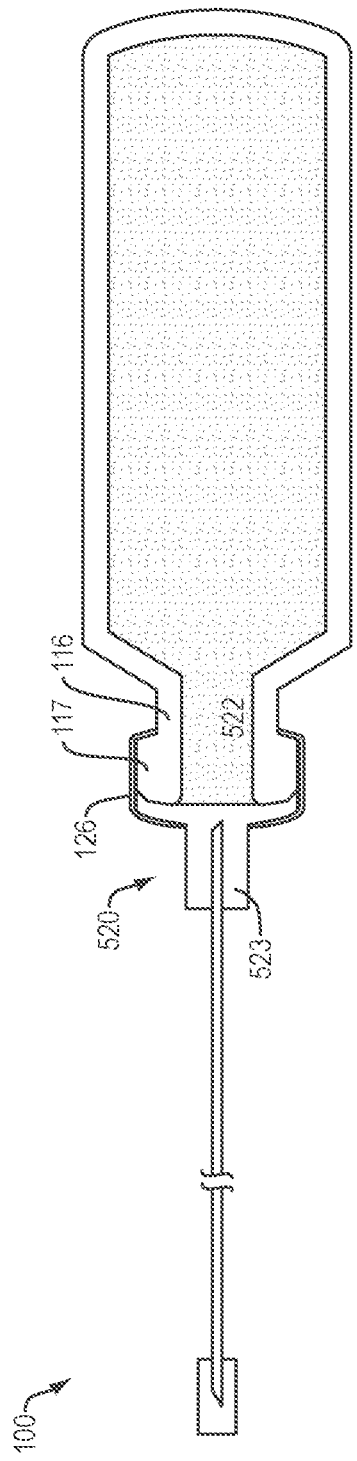
FIG. 5 provides a schematic view of an alternative single-barrier drug delivery system, according to one embodiment of the present disclosure.

This disclosure presents various systems, components, and methods related to a drug delivery system and/or the sterilization of the drug delivery system. Each of the systems, components, and methods disclosed herein provides one or more advantages over conventional systems, components, and methods.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which this disclosure belongs.

Although embodiments of the present disclosure are described with specific reference to drug delivery, the systems and methods disclosed herein may be used to provide a sterile fluid path for a variety of sterile solutions, agents, materials, biological and/or pharmaceutical compositions from a variety of containers, cartridges, syringes, pens, needles and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the terms "proximal" and "distal" refer to opposite portions of the devices or systems described herein, with "proximal" generally referring to the portion closest to the user of the devices or systems.

The present disclosure provides various drug delivery systems that include a drug-loaded container attached to a fluid path (e.g., transfer tube, needle, syringe, etc.) by a cap (e.g., plug, stopper, septum, etc.). As used herein, "drug" refers to any therapeutic agent administered to a user, as described herein. As used herein, "container" refers to any suitable space for containing a fluid drug. The cap may be configured to seal an opening of the container and establish sufficient separation between the fluid path and drug such that sterilization energy applied to a distal portion of the fluid path does not contact or otherwise act upon any portion of the drug.

Various embodiments provide drug delivery systems that can provide a fluid path and a drug container holding a liquid drug. The fluid path can be sterilized by an energy source without disturbing the liquid drug, which can be sterilized prior to sterilizing the fluid path. The fluid path can be coupled to the container such that after sterilization, the drug delivery system is immediately ready for use. Upon activation, for example based on a user input, the fluid path can be coupled to the stored liquid drug, thereby providing a route for delivery of the liquid drug to the user. The systems and methods described herein obviates the need for a user to transfer a liquid drug to a drug delivery system prior to use and also obviates the need for a user to assemble a drug delivery device prior to use—accordingly, embodiments provided herein provide fully assembled ready to use drug delivery systems through the arrangements and sterilizations techniques described herein.

Single-Barrier Systems

Referring to FIG. 1, in one embodiment, a drug delivery system 100 of the present disclosure may include, in combination, a container 112, a cap 120 and a fluid path 140. The container 112 may include a body 114 and a neck 116 defining an interior region 118. The cap 120 may be disposed about at least a portion of the neck 116 to contain a fluid drug 150 within the interior region 118. The fluid path 140 (e.g., transfer tube, needle, syringe, etc.) may define a lumen 146 and further include a first portion 142 with a sharpened first end 141, and a second portion 144 with a sharpened second end 143.

The cap 120 may include a "top hat" configuration secured to the neck 116 by a first crimp 126. For example, the cap 120 may include a first portion 122 configured to extend at least partially into the neck 116, a second portion 123 configured to overlap an end of the neck 116 and a third portion 124 configured to extend distally beyond (e.g., away from) the second portion 123. The neck 116 may include a flared portion 117 to provide a surface against which the first crimp 126 may be compressed to secure the second portion 123 of the cap 120 against the end of the neck 116. The first crimp 126 may include any suitably deformable and/or compressible material (e.g., metals, alloys, plastics, rubbers, and the like), as are known in the art. In various embodiments, the cap 120 may be secured to the neck 116 by a variety of additional and/or alternative attachment mechanisms, including, by way of non-limiting example, corresponding threaded or luer-lock surfaces, adhesives, glues, solders, resins and the like.

The first portion 142 of the fluid path 140 may be disposed (e.g., embedded, housed, etc.) within the third portion 124 of the cap 120 such that the sharpened first end 141 is maintained a pre-determined distance away from the interface between the fluid drug 150 and the first portion 122 of the cap 120. For example, the sharpened first end 141 of the fluid path 140 may be separated from the fluid drug 150 by a distance of 10 cm or more, more preferably 20 cm or more, and even more preferably 30 cm or more. The third portion 124 of the cap 120 may also provide structural support to the first portion 142 of the fluid path 140, thereby preventing bending and/or moving of the fluid path during shipping, storage and/or use, which might comprise the integrity of the fluid-tight seal. In one embodiment, the first portion 142 of the fluid path 140 may be disposed within a channel 125 formed within the third portion 124 of the cap 120 to reduce or eliminate the potential for the lumen 146 to become plugged with a "core" of the cap 120 as the fluid path 140 is advanced into the interior region 118. Although the channel 125 is depicted as extending through the length of the third portion 124, in various embodiments the channel 125 may extend through a portion of the third portion 124. In addition, or alternatively, the channel 125 may extend through the third portion 124 into the first or second portions 122, 123 of the cap 120.

The second portion 144 of the fluid path 140 may be disposed (e.g., embedded, housed, etc.) within a cover 148 such that the sharpened second end 143 is shielded prior to use. In one embodiment, a length of the second portion 144 may be sufficient to penetrate the dermal layer of a patient. For example, the second portion 144 of the fluid path 140 may have a length of 0.5 cm or more, more preferably 1.0 cm or more, and even more preferably 2.0 cm or more.

Referring to FIG. 2, in one embodiment, a drug delivery system 100 of the present disclosure may further include a cap 220 with a "top hat" configuration like that of FIG. 1, with a first portion 222 configured to extend at least half-way (e.g., approximately 50%) into the neck 116 to provide additional separation between the first portion 142 (and sharpened first end 141) of the fluid path 140 and the fluid drug 150 within the interior region 118 of the container 112. In various embodiments, the first portion 222 may extend more than half-way into the neck 116, including, for example, extending completely (e.g. 100%) into the neck.

Referring to FIG. 3, in one embodiment, a drug delivery system 100 of the present disclosure may further include a cap 320 which includes a first portion 322 configured to extend at least half-way (e.g., approximately 50%) into the neck 116, and a second portion 323 configured to overlap an end of the neck 116, without a corresponding third portion extending distally beyond the second portion 323. The neck 116 may include a flared portion 117 to provide a surface against which the first crimp 126 may be compressed to secure the second portion 323 of the cap 320 against the end of the neck 116.

Referring to FIGS. 4A-4C, in one embodiment, a drug delivery system 100 of the present disclosure may further include a cap 420 with a "top hat" configuration like that of FIG. 1, with a third portion 424 configured to extend distally beyond (e.g., away from) a second portion 423, and a first portion 422 configured to extend at least partially into the neck 116. The third portion 424 may include a chamber 429 which defines an open area or space configured to house the first portion 142 of the fluid path 140 (FIG. 4A). The open area or space defined by the chamber 429 may provide various benefits as compared to a completely solid cap. For example, the chamber 429 may reduce the amount of resistance required to advance the first portion 142 of the fluid path 140 into the interior region 118 of the container 112 (FIG. 4B). In addition, the chamber 429 may extend proximally beyond the sharpened first end 141 of the fluid path 140 to further reduce or eliminate the potential for the lumen 146 to become plugged with a "core" of the cap 420 as the fluid path 140 is advanced in the direction of the arrow 105 into the interior region 118. In addition, or alternatively, the chamber 429 may reduce the amount of resistance required to advance the first portion 142 of the fluid path 140 in the direction of the arrow 105 into the interior region by moving to a collapsed configuration (FIG. 4C). Although the chamber 429 is depicted entirely within the third portion 424 of the cap 420, in various embodiments, the chamber 429 may extend into the second portion 423 or first portion 422 of the cap 420.

Referring to FIG. 5, in one embodiment, a drug delivery system 100 of the present disclosure may further include a cap 520 with a "top hat" configuration, which includes a first portion 522 configured to overlap an end of the neck 116, and a second portion 523 configured to extend distally beyond (e.g., away from) the neck 116, without any portion of the cap extending into the neck 116. The neck 116 may include a flared portion 117 to provide a surface against which the first crimp 126 may be compressed to secure the first portion 522 of the cap 520 against the end of the neck 116.

In any of the embodiments of FIGS. 1-4C, the first portion 122, 222, 322, 422 of the respective cap 120, 220, 320, 420, which extends into the neck 116 may include one or more compliant or semi-compliant materials, as are known in the art (e.g., polymers, rubbers, silicones, etc.), which are sufficiently compressible to establish a friction or interference fit with an inner wall of the neck 116 with sufficient force to resist movement (e.g., creeping) of the cap, and provide a fluid-tight seal. In addition, at least the interface surface of the first portion 122, 222, 322, 422, 522 of the cap 120, 220, 320, 420, 520, which contacts the fluid drug 150 may preferably include a material which is compatible with (e.g., does not react with or otherwise alter) the fluid drug 150.

As illustrated in FIG. 1, in any of the embodiments of FIGS. 1-5, a length $L_1$ of the first portion 142 of the fluid path 140 disposed within the cap 120 may be greater than a distance $L_2$ between the sharpened first end 141 and an interface of the fluid drug 150 and the first portion 122 of the cap 120. As will be understood by those of skill in the art, the length $L_1$ may be sufficient to allow only the first portion 142 of the fluid path 140 embedded within the cap 120 to be placed in contact with the fluid drug 150 when the fluid path 140 is advanced, thereby preventing a potentially non-sterile portion of the fluid path 140 extending distally beyond the cap 120 from contacting the fluid drug 150. As will be understood by one of skill in the art, single-barrier system embodiments of FIGS. 1-5 may include a cap to maintain separation between the portion of the fluid path disposed within the cap (including the first sharpened end) and the fluid drug inside the container.

Double-Barrier Systems

Figure 6:
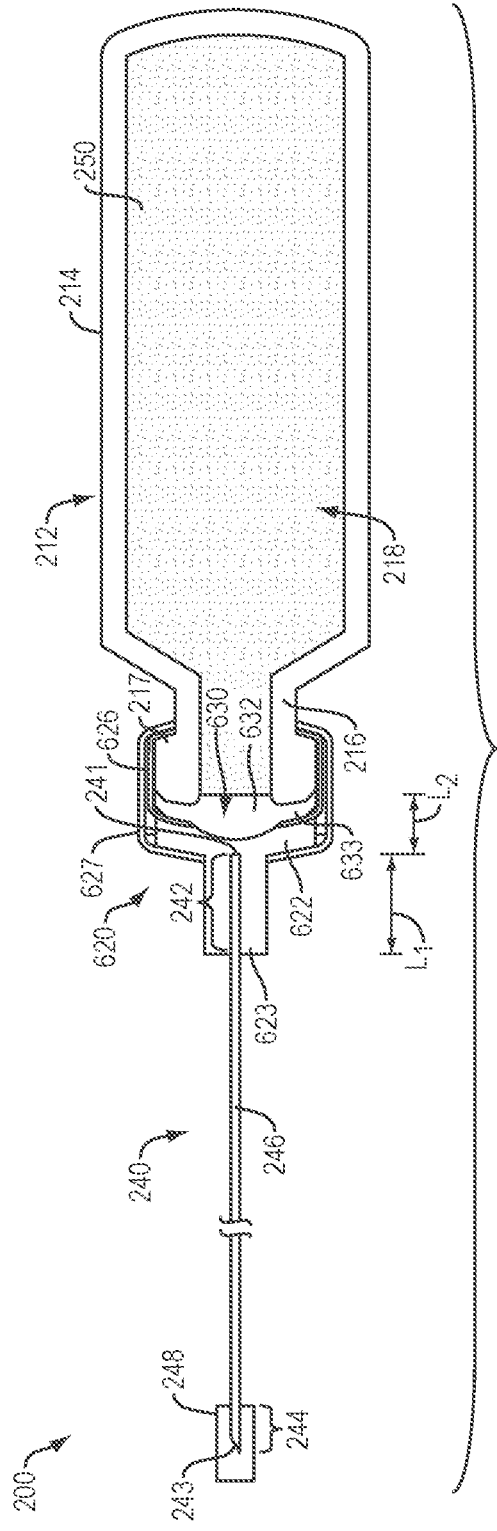
FIG. 6 provides a schematic view of a double-barrier drug delivery system, according to one embodiment of the present disclosure.

Referring to FIG. 6, in one embodiment, a drug delivery system 200 of the present disclosure may include, in combination, a container 212, a septum 630, a cap 620 and a fluid path 240. The container 212 may include a body 214 and a neck 216 defining an interior region 218. The septum 630 may be disposed about at least a portion of the neck 216 to retain a fluid drug 250 (e.g., drug, biological composition, pharmaceutical composition, etc.) within the interior region 218. The cap 620 may be disposed against at least a portion of the septum 630. The fluid path 240 (e.g., transfer tube, needle, syringe, etc.) may define a lumen 246 and further include a first portion 242 with a sharpened first end 241, and a second portion 244 with a sharpened second end 243.

The septum 630 may be secured to the neck 216 by a first crimp 626. For example, the septum 630 may include a first portion 632 configured to extend at least partially into the neck 216, and a second portion 633 configured to overlap an end of the neck 216. The neck 216 may include a flared portion 217 to provide a surface against which the first crimp 626 may be compressed to secure the second portion 633 of the septum 630 against the end of the neck 216. The first crimp 626 may include any suitably deformable and/or compressible material (e.g., metals, alloys, plastics, rubbers, and the like), as are known in the art. Although the first portion 632 of the septum 630 is depicted as extending into a portion of the neck 216, in various embodiments, the first portion 632 may extend into the entire portion (e.g., 100%) of the neck, less than the entire portion of the neck (e.g., approximately 50%), no portion (e.g., 0%) of the neck, or any variation thereof. The septum 630 may include one or more compliant or semi-compliant materials, as are known in the art (e.g., polymers, rubbers, silicones, etc.), which are sufficiently compressible (e.g., crimpable) to establish a fluid-tight seal between an inner surface of the first crimp 626 and the end of the neck 216. In addition, at least the portion (e.g., interface surface) of the septum 630, which contacts a fluid drug 250 may preferably include a material which is compatible with (e.g., does not react with or otherwise alter) the fluid drug 250.

The cap 620 may be secured to the neck 216 by a second crimp 627 disposed around a portion of the first crimp 626. For example, the cap 620 may include a "top hat" configuration which includes a first portion 622 configured to overlap at least a portion of the septum 630 and the first crimp 626, and a second portion 623 configured to extend distally beyond (e.g., away from) the first portion 622. The second crimp 627 may include any suitably deformable and/or compressible material (e.g., metals, alloys, plastics, rubbers, and the like), as are known in the art. In various embodiments, the cap 620 may be secured to the septum 630 by a variety of additional and/or alternative attachment mechanisms, including, by way of non-limiting example, corresponding threaded or luer-lock surfaces, adhesives, glues, solders, resins and the like.

The first portion 242 of the fluid path 240 may be disposed (e.g., embedded, housed, etc.) within the second portion 623 of the cap 620 such that the sharpened first end 241 is maintained a pre-determined distance away from the interface between the fluid drug 250 and the first portion 632 of the septum 630. For example, the sharpened first end 241 of the fluid path 240 may be separated from the fluid drug 250 by any distance, including but not limited to, 10 cm or more, more preferably 20 cm or more, and even more preferably 30 cm or more. The second portion 623 of the cap 620 may also provide structural support to the first portion 242 of the fluid path 240, thereby preventing bending and/or moving of the fluid path during shipping, storage and/or use, which might comprise the integrity to the fluid-tight seal.

The second portion 244 of the fluid path 240 may be disposed (e.g., embedded, housed, etc.) within a cover 248 such that the sharpened second end 243 is shielded prior to use. In one embodiment, a length of the second portion 244 may be sufficient to penetrate the dermal layer of a patient. For example, the second portion 244 of the fluid path 240 may have a length of 0.5 cm or more, more preferably 1.0 cm or more, and even more preferably 2.0 cm or more.

Referring to FIG. 7, in one embodiment, a drug delivery system 200 of the present disclosure may further include a cap 720 with a "top hat" configuration like that of FIG. 6, which includes a first portion 722 configured to overlap at least a portion of the septum 730 and the first crimp 726, and a second portion 723 configured to extend distally beyond (e.g., away from) the first portion 722. The first and second portions 722, 723 may include a chamber 729 which defines an open area or space configured to house the first portion 242 of the fluid path 240. The open area or space defined by the chamber 729 may provide various benefits as compared to a completely solid cap. For example, the chamber 729 may reduce the amount of resistance required to advance the first portion 242 of the fluid path 240 into the interior region 218 of the container 212. In addition, as compared to embodiments in which the first portion of the fluid path is embedded within the cap, the chamber 729 may reduce or eliminate the potential for the lumen 246 to become plugged with a "core" of the cap 720 as the fluid path 240 is advanced into the interior region 218. In addition, or alternatively, the chamber 729 may reduce the amount of resistance required to advance the first portion 242 of the fluid path 240 into the interior region 218 by moving to a collapsed configuration (not shown). Although the chamber 729 is depicted as extending between the first and second portions 722, 723, in various embodiments, the chamber may be formed entirely within the second portion 723 of the cap 720. Referring to FIG. 8, in one embodiment, a drug delivery system 200 of the present disclosure may further include one or more O-rings 828 disposed between the septum 830 and first portion 822 of a cap 820 to maintain a fluid-tight seal about the neck 216.

In any of the embodiments of FIGS. 1-8, the cap 120, 220, 320, 420, 520, 620, 720, 820, may include a dual-durometer material. For example, a portion of the cap may include a high durometer material, e.g., to provide additional support to the fluid path and/or provide a firm surface against which the first or second crimps may press for improved sealing. Another portion of the cap may include a low durometer material, e.g., to reduce or eliminate coring and/or provide improved sealing as the fluid path is advanced into the interior region of the container. In addition, at least a portion of the cap may include a material that is compatible with the specific sterilization modality employed (e.g., does not degrade or otherwise break down), as discussed below.

As illustrated in FIG. 6, in any of the embodiments of FIGS. 6-8, a length $L_1$ of the first portion 242 of the fluid path 240 disposed within the cap 220 may be greater than a distance $L_2$ between the sharpened first end 241 and an interface of the fluid drug 250 and the first portion 632 of the septum 630. As will be understood by those of skill in the art, the length $L_1$ may be sufficient to allow only the first portion 242 of the fluid path 240 embedded within the cap 220 to be placed in contact with the fluid drug 250 when the fluid path 240 is advanced, thereby preventing a potentially non-sterile portion of the fluid path 240 extending distally beyond the cap 220 from contacting the fluid drug 250. As will be understood by one of skill in the art, double-barrier system embodiments of FIGS. 6-8 may include a cap and/or septum to maintain separation between the portion of the fluid path disposed within the cap (including the first sharpened end) and the fluid drug inside the container.

Although the drug delivery systems disclosed herein generally include a cap (FIGS. 1-5) or cap and septum (FIGS. 6-8) attached to the neck of a container, in various embodiments the container may include a variety of shapes and or configurations (e.g., cartridges, vials, pens, etc.) that do not necessarily include a neck.

Sterilization Protocols

Figure 9:
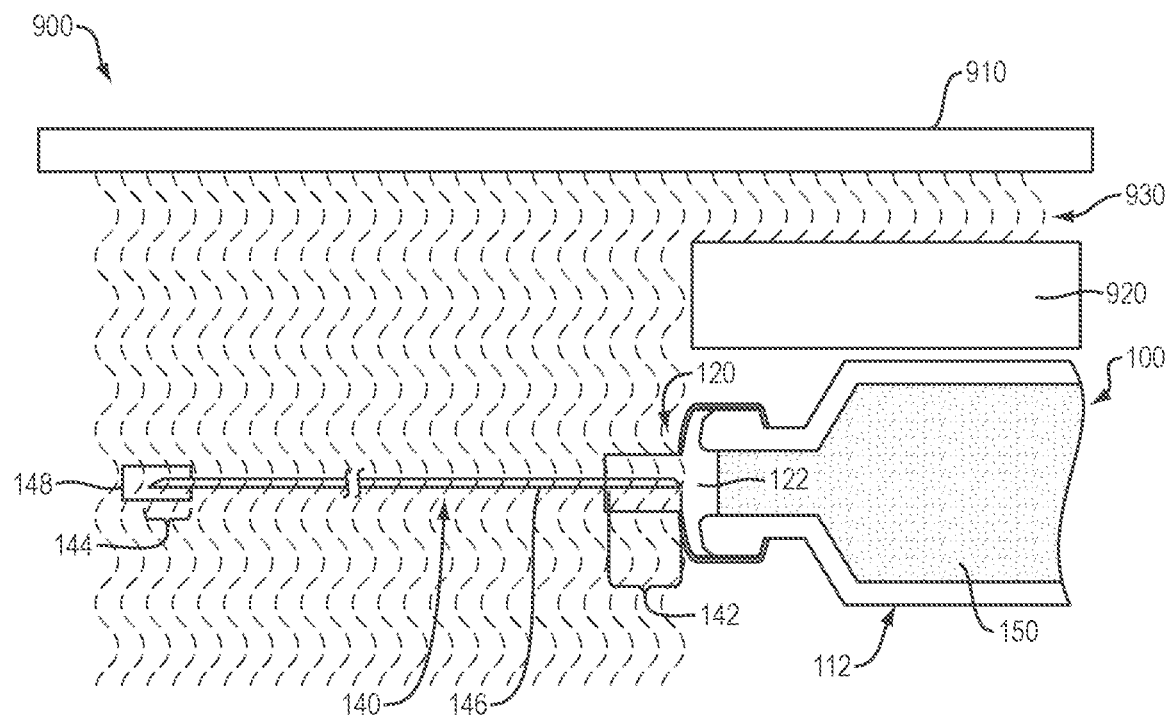
FIG. 9 provides a schematic view of a sterilization system using a single-barrier drug delivery system, according to one embodiment of the present disclosure.

In one embodiment, any of the drug delivery systems disclosed herein may undergo a sterilization protocol to provide a sealed and sterile fluid path. Referring to FIG. 9, a drug delivery system 100, 200 may be placed within a sterilization system 900, which includes an energy source 910 and a shield 920. In various embodiments, the energy source 910 may emit x-ray, γ-ray or electrical-beam (e.g., e-beam) energy. The shield 920 may include a material with a suitable composition and/or thickness to prevent (e.g., block) energy emitted 930 from the energy source 910 from passing (e.g., penetrating) therethrough. In various embodiments, the shield may comprise a material which does not emit or generate energy (e.g. x-rays, etc.) when acted upon by an energy source (or limits such emissions). For example, the shield may be formed partially or entirely of aluminum having a thickness of approximately 30 mm or more.

The energy source 910 and shield 920 may be positioned relative to each other such that a portion of the energy emitted 930 from energy source 910 contacts and is blocked by the shield 920, and another portion of the energy emitted 930 is direct beyond an end of the shield 920 and remains unblocked. Alternatively, the shield 920 may include an opening (not shown) such that the energy emitted 930 from the energy source 910 contacts and is blocked by the shield 920 on either side of the opening. By way of example, the drug delivery system 100 may be positioned within the sterilization system 900 such that the entire portion of the container 112 which contains the fluid drug 150, and at least part of the first portion 122 of the cap 120, is aligned with (e.g., underneath) the shield 920 and protected from the energy emitted 930 from the energy source 910.

The remaining portion of the drug delivery system 100, including the cover 148, entire fluid path 140, and at least the portion of the cap 120 disposed around the first portion of the 142 of the fluid path 140, is not aligned with (e.g., extends beyond) the shield 920. Upon activation of the energy source 910, the emitted energy 930 passes through and sterilizes the entire unshielded portion of the drug delivery system 100, including the first portion 142 of the fluid path 140 embedded within the cap 120, the second portion 144 of the fluid path 140 embedded within the cover 148 and the lumen 146 extending therebetween, thereby providing a sterile and sealed fluid path. Since the energy source 910 does not generate heat, the drug delivery system 100 may remain within the sterilization system 900 as long as required for sterilization of the entire fluid path 140 without the need for any form of refrigeration, light and/or humidity control systems. As explained above, various cap (and septum) configurations may be used to increase or decrease the distance between the portion of the fluid path embedded within the cap and the fluid drug within the container depending, e.g., on the preferred target surface area for the energy source, the duration of the sterilization protocol and/or the stability requirements of the specific fluid. Although FIG. 9 depicts a drug delivery system 100 of the present disclosure undergoing a sterilization protocol, in various embodiments, any of the drug delivery systems disclosed herein 200, 300, 400 may undergo a sterilization protocol in a sterilization system of FIG. 9 or FIGS. 16-18 (discussed below).

In various embodiments herein, the drug stored in the container can be exposed to limited amounts of the emitted energy (e.g., radiation or electron beam). The amount of exposure can be less than a critical level and/or less than a level that can cause substantial degradation of the drug stored in the container.

As will be understood by one of skill in the art, the drug delivery systems, sterilization systems and protocols described herein may provide a number of advantages over conventional drug delivery systems, sterilization systems and modalities. By way of a non-liming example, the disclosed sterilization systems and protocols may be temperature independent, thereby allowing sterilization to be performed in a cold (e.g., refrigerated) environment to prevent degradation or inactivation of temperature sensitive drugs, biological and/or pharmaceutical compositions. In addition, the ability of the disclosed sterilization systems and protocols to be performed at the ideal temperature for a specific drug, biological and/or pharmaceutical composition, may eliminate the need for special formulations to be compatible. The disclosed drug delivery devices, sterilization systems and protocols may also eliminate the need for specialized environmental conditions (e.g., vacuum sealed containers, etc.). The disclosed drug delivery devices, sterilization systems and protocols may also prevent exposure of the biological and/or pharmaceutical composition, as well as certain material components of the drug-delivery system, to the specific sterilization modality (x-ray, γ-ray or electrical-beam (e.g., e-beam) energy). The disclosed sterilization systems and protocols may also be compatible with conventional containers, thereby eliminating the need to exchange containers during the filling or finishing process.

Figure 10:
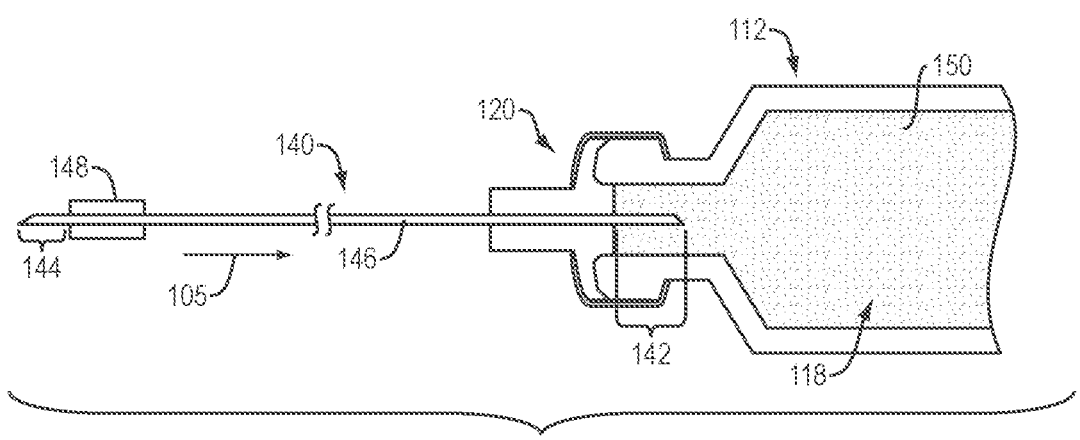
FIG. 10 provides a schematic view of an activated single-barrier drug delivery system, according to one embodiment of the present disclosure.

Referring to FIG. 10, in use and by way of example, a user may "activate" a drug delivery system by proximally advancing the fluid path 140 in the direction of the arrow 105 towards the container 112 such that the sterile first portion 142 of the fluid path 140 housed within the cap 120 enters the interior region 118. With the lumen 146 of the fluid path 140 in contact with the fluid drug 150, the sterile second portion 144 of the fluid path 140 may be advanced through the cover 148 and dermal layer of the patient. Since only the first and second portions 142, 144 of the fluid path 140 penetrate the interior region 118 of the container 112 and the dermal layer, respectively, any non-sterile portion of the fluid path 140 (e.g., between the cap 120 and cover 148) is prevented from penetrating either the patient or the container. In one embodiment, the steps of advancing the first portion 142 of the fluid path 140 into the interior region 118 of the container 112, and advancing the second portion 144 of the fluid path 140 through the dermal layer, may occur almost simultaneously. For example, a user may employ a "jabbing" or "stabbing" motion to advance the sterile second portion 144 of the fluid path 140 into the dermal layer. The force exerted on the fluid path 140 by this "jabbing" or "stabling" motion may simultaneously drive the sterile first portion 142 of the fluid path 140 into the interior region 118 of the container 112. In one embodiment, the container 112 may be pressurized such that the proper dosage of fluid drug 150 is automatically delivered through the lumen 146 of the fluid path 140 and into the patient. Alternatively, the container 112 may include a delivery mechanism, e.g., plunger, etc. (not shown) which the user may actuate as necessary to deliver the fluid drug 150 through the lumen 146 of the fluid path 140 and into the patient. Alternatively, the drug delivery system may include an inertia driven system that includes, e.g., a safety and trigger mechanism configured to automatically drive the first portion 142 of the fluid path 140 into the interior region 118 of the container and/or drive the second portion 144 of the fluid path 140 through the dermal layer. In various embodiments, the drive/delivery mechanism which conveys movement of the fluid path in either (or both) directions may include an electromechanical or mechanical system.

Assembly Protocols

Prior to implementing the sterilization protocol, the drug delivery systems of the present disclosure may undergo various assembly protocols using aseptic techniques, as are known in the art. For example, a drug delivery system 100 that includes a single-barrier may be assembled by sterilizing the container 112 with ethylene oxide, and sterilizing the cap 120 with steam or γ-irradiation. In some embodiments, the cap may comprise a gas-permeable material compatible with nitrous oxide ($NO_2$) sterilization, which may be beneficial for sterilizing a cap that includes an inner chamber. The sterilized container 112 may then be filled with a sterile fluid drug 150 under aseptic conditions. The sterilized cap 120 may then be positioned on the neck 116 of the fluid-filled container 112 and secured using the first crimp 126. Alternatively, the sterilized cap 120 may be attached to an empty sterilized container 112, as outlined above, and the container 112 filled with sterile fluid drug 150 through the cap 120 using a sterile syringe. The first portion 142 of the fluid path 140 may then be positioned (e.g., inserted) a predetermined distance within the cap 120, and the second portion 144 of the fluid path 140 may be positioned a predetermined distance within a cover 148.

A drug delivery system 200 that includes a double-barrier system may be assembled by sterilizing the container 212 with ethylene oxide, and sterilizing the cap 620, 720, 820 and septum 630, 730, 830 with steam or γ-irradiation. The container 212 may then be filled with sterile fluid drug 250 under aseptic conditions. The sterilized septum 630, 730, 830 may then be positioned on the neck 216 of the fluid-filled container 212 and secured using the first crimp 626. Alternatively, the sterilized septum 630, 730, 830 may be attached to an empty sterilized container 212, as outlined above, and the container 212 filled with the fluid drug 250 through the septum 630, 730, 830 using a sterile syringe. The sterilized cap 620, 720, 820 may then be positioned on or above the septum 630, 730, 830 and secured using the second crimp 627. The first portion 242 of the fluid path 240 may then be positioned (e.g., inserted) a predetermined distance within the cap 620, 720, 820 and the second portion 244 of the fluid path 240 may be positioned a predetermined distance within the cover 248. The fully assembled drug delivery system 100, 200 may then undergo a sterilization protocol to provide a sealed and sterile fluid path, as discussed above.

Plunger Systems

In various embodiments, a drug delivery system of the present disclosure may include a needle path that does not extend through the cap and/or septum positioned at the neck of the container, but instead extends through a cap and plunger located at the opposite end of the container. The container may be filled under aseptic conditions by introducing the needle of a separate syringe (not shown) through the septum into the interior region 118.

Referring to FIG. 11, in one embodiment, a drug delivery system 300 of the present disclosure may include, in combination, a container 312, a cap 1120, a plunger 1160 and a fluid path 340. The container 312 may include a body 314 defining an interior region 318. The cap 1120 may be disposed within an end portion of the container 312. The fluid path 340 (e.g., transfer tube, needle, syringe, etc.) may define a lumen 346 and further include a first portion 342 with a sharpened first end 341, and a second portion 344 with a sharpened second end 343. The cap 1120 may include one or more semi-compliant materials, as are known in the art (e.g., polymers, rubbers, silicones, etc.), which are sufficiently compressible to establish a friction or interference fit with an inner wall of the container 312 with sufficient force to resist movement of the cap, and provide a fluid-tight seal. The cap 1120 may further include one or more O-rings 1128 disposed between the cap 1120 and inner wall of the container 312 to maintain the fluid-tight seal. A septum 1130 may be disposed within, and extend through, a central portion of the cap 1120. The septum 1130 may be permanently affixed within the cap 1120 using suitable adhesives, glues and/or resins, as are known in the art.

Alternatively, in place of a septum, the cap 1120 may include a dual-durometer material such that, e.g., an outer portion of the cap 1120 is formed of a high-durometer material for improved compression against the inner wall of the container 312, and an inner portion of the cap 1120 is formed of a low-durometer material to reduce or eliminate coring and/or provide improved sealing around the fluid path 340. The cap 1120 and/or septum 1130 may also provide structural support to the first portion 342 of the fluid path 340, thereby preventing bending and/or moving of the fluid path during shipping, storage and/or use, which might comprise the integrity of the fluid-tight seal. In addition, at least a portion of the plunger 1160, cap 1120 and/or septum 1130 may include a material that is compatible with the specific sterilization modality employed (e.g., does not degrade or otherwise break down), as discussed above.

The plunger 1160 may be slidably disposed within the container 312 proximal to the septum to retain a fluid drug 350 (e.g., drug, biological composition, pharmaceutical composition, etc.) within the interior region 318. The first portion 342 of the fluid path 340 may be disposed within an open space 362 between the cap 1120 and plunger 1160 such that the sharpened first end 341 is maintained a predetermined distance away from the interface between the fluid drug 350 and the plunger 1160. For example, the sharpened first end 341 of the fluid path 340 may be separated from the fluid drug 350 by a distance of 10 cm or more, more preferably 20 cm or more, and even more preferably 30 cm or more. The second portion 344 of the fluid path 340 may be disposed (e.g., embedded, housed, etc.) within a cover 348 such that the sharpened second end 343 is shielded prior to use. In one embodiment, a length of the second portion 344 may be sufficient to penetrate the dermal layer of a patient. For example, the second portion 344 of the fluid path 340 may have a length of 0.5 cm or more, more preferably 1.0 cm or more, and even more preferably 2.0 cm or more.

Referring to FIG. 12, in one embodiment, the first portion 342 of the fluid path 340 may extend through the open space 362 into a portion of the plunger 1160 to provide additional support and/or protection to the fluid path.

In various embodiments, the drug delivery system 300 may be positioned within a sterilization system, as discussed above, such that the entire portion of the container 312 which contains the fluid drug is aligned with (e.g., underneath) a shield and protected from energy emitted from an energy source. The remaining portion of the drug delivery system 300, including the first portion 342 of the fluid path 340 and at least a portion of the plunger 1160, is not aligned with (e.g., extends beyond) the shield. Upon activation of the energy source, the emitted energy passes through and sterilizes the entire unshielded portion of the drug delivery system 300 (e.g., the first portion 342 of the fluid path 340 and a portion of the plunger 1160), thereby providing a sterile and sealed fluid path. In various embodiments, the first portion 342 of the fluid path 340 can be positioned within a portion of the plunger 1160. In such embodiments, the first portion 342 of the fluid path 340 can be partially embedded in the plunger 1160. The first portion 342 of the fluid path 340 can be exposed to emitted energy from the energy source for sterilization. After sterilization, upon activation, the first portion 342 of the fluid path 340 can pierce through the remaining portion of the plunger 1160.

The individual components (e.g., container 312, cap 1120, septum 1130 and plunger 1160) of the drug delivery system 300 of FIG. 11 or 12 may be individually sterilized, assembled and filled with fluid drug 350 using aseptic techniques, as described above. Similarly, the drug delivery systems 300 of FIG. 11 or 12 may undergo a sterilization protocol which shields the portion of the container 312 filled with the fluid drug 350 and exposes the full length of the fluid path 340 to sterilization energy to provide a sealed and sterile fluid path 340, as described above.

Figure 13:
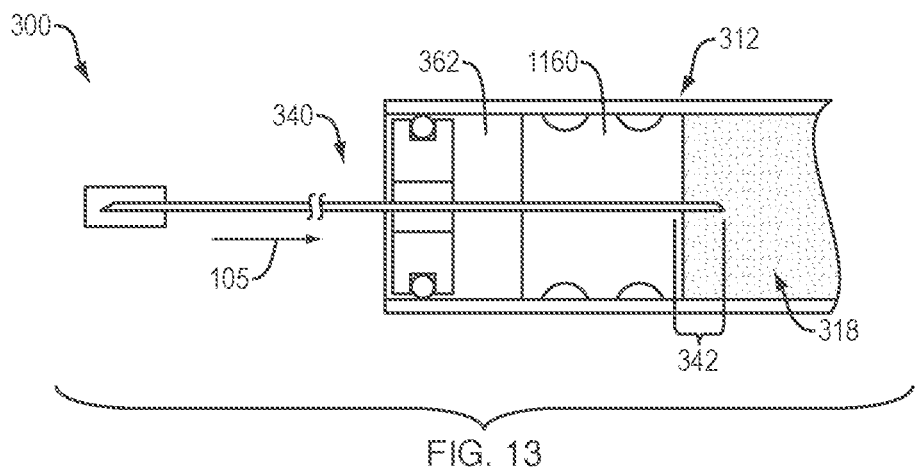
FIG. 13 provides a first schematic view of an activated plunger drug delivery system, according to one embodiment of the present disclosure.
Figure 14:
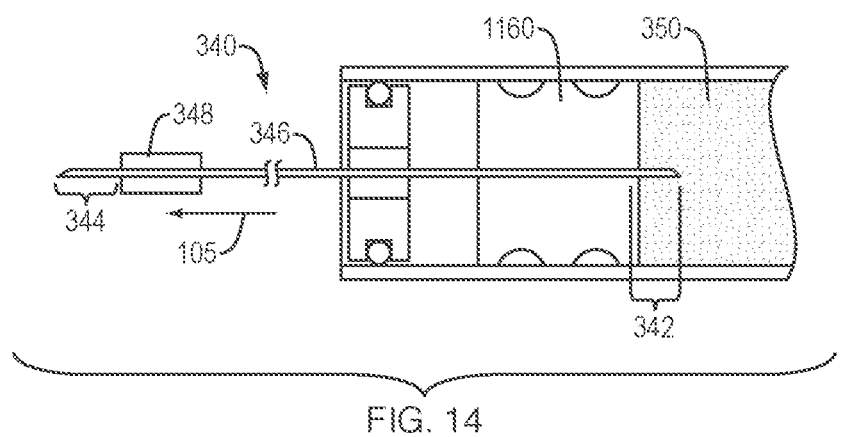
FIG. 14 provides a second schematic view of an activated plunger drug delivery system, according to one embodiment of the present disclosure FIG. 15A provides a first schematic view of a pre-loaded syringe drug delivery system, according to one embodiment of the present disclosure.

Referring to FIG. 13, in use and by way of example, a user may "activate" a drug delivery system 300 by proximally advancing the fluid path 340 in the direction of the arrow 105 towards the container 312 such that the sterile first portion 342 of the fluid path 340 housed within the open space 362 (FIG. 11) or plunger 1160 (FIG. 12) enters the interior region 318. Referring to FIG. 14, with the lumen 346 the fluid path 340 in contact with the fluid drug 350, the sterile second portion 344 of the fluid path 340 may be advanced in the direction of the arrow 105 through the cover 348 to penetrate the dermal layer of the patient, and the plunger 1160 and fluid path 340 advanced proximally to force the fluid drug 350 through the lumen 346 of the fluid path 340 into the patient. Since only the first and second portions 342, 344 of the fluid path 340 penetrate the interior region 318 of the container 312 and dermal layer, respectively, any non-sterile portion of the fluid path 340 (e.g., between the cap 320 and cover 348) is prevented from penetrating either the patient or the container.

In any of the embodiments of FIGS. 11 and 12, a length $L_1$ of the first portion 342 of the fluid path 340 disposed within the open space 362 (FIG. 11) or plunger 1160 (FIG. 12) may be greater than a distance $L_2$ between the sharpened first end 341 and an interface of the fluid drug 350 and the plunger 1160. As will be understood by those of skill in the art, the length $L_1$ may be sufficient to allow only the first portion 342 of the fluid path 340 embedded within the open space 362, or plunger 1160, to be placed in contact with the fluid drug 350 when the fluid path 340 is advanced proximally, thereby preventing a potentially non-sterile portion of the fluid path 340 extending distally beyond the open space 362 or plunger 1160 from contacting the fluid drug 350.

Pre-Loaded Syringe Systems

Figure 15A:
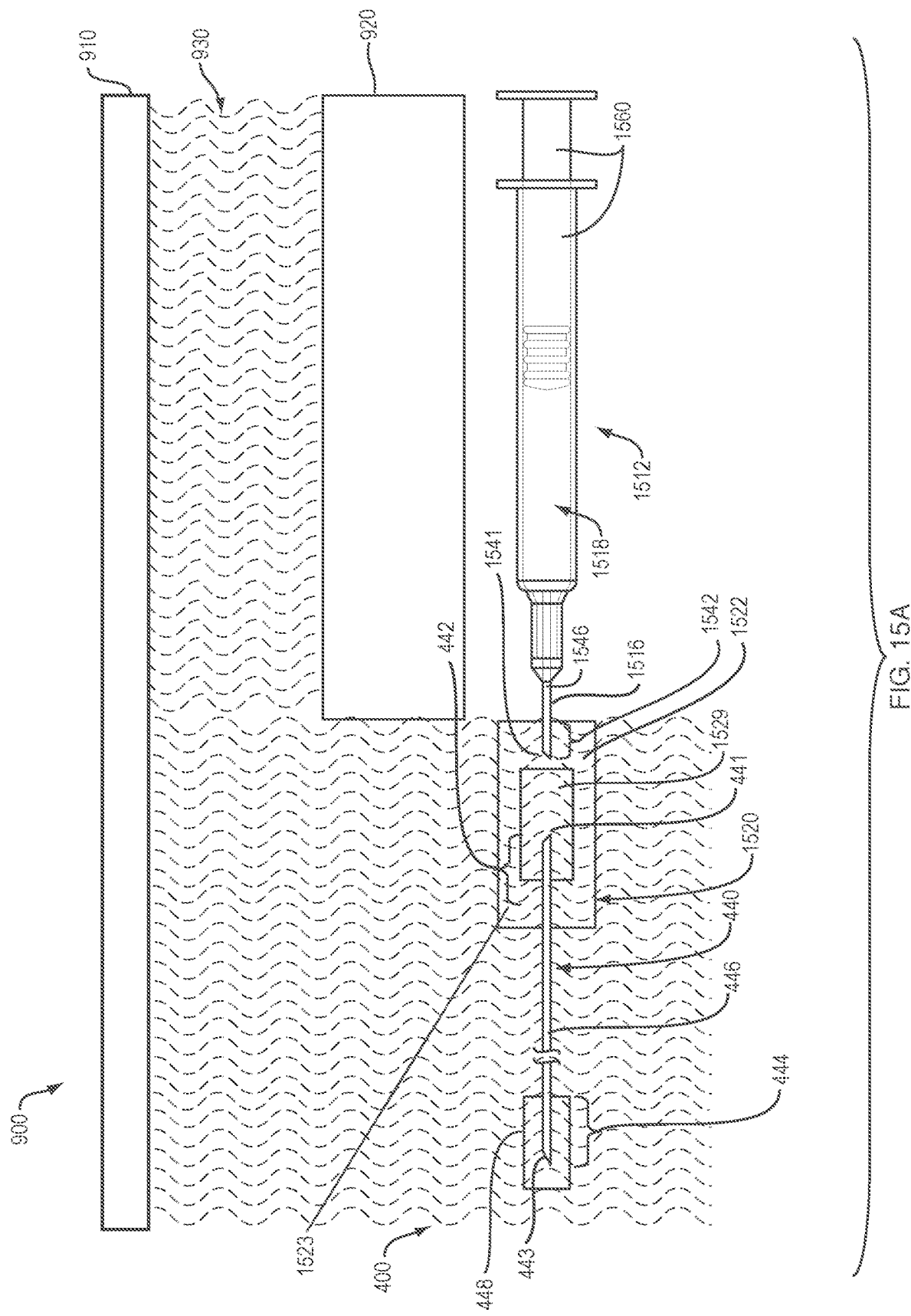
FIG. 15B provides a second schematic view of a pre-loaded syringe drug delivery system, according to one embodiment of the present disclosure.

Referring to FIG. 15A, in one embodiment, a drug delivery system 400 of the present disclosure may include, in combination, a container 1512, a cap 1520 and a fluid path 440. The container 1512 may include, e.g., a standard syringe comprising a needle 1516 in fluid communication with an interior region 1518 of the container and a plunger 1560 slidably disposed within the interior region 1518. The needle 1516 may define a lumen 1546 and further include a distal portion 1542 with a sharped end 1541. The distal portion 1542 of the needle 1516 may be embedded within a first portion 1522 of the cap 1520. The fluid path 440 (e.g., transfer tube, needle, syringe, etc.) may define a lumen 446 and further include a first portion 442 with a sharpened first end 441, and a second portion 444 with a sharpened second end 443. The first portion 442 of the fluid path 440 may extend through a second portion 1523 of the cap 1520 and into a chamber 1529 within the cap 1520. The second portion 444 of the fluid path 440 may be disposed (e.g., embedded, housed, etc.) within a cover 448 such that the sharpened second end 443 is shielded prior to use.

The container 1512 may be sterilized using ethylene oxide, steam or γ-irradiation and loaded with a sterile fluid drug 450 using aseptic techniques, as described above. The distal portion 1542 of the needle 1516 and first portion 442 of the fluid path 440 may then be positioned within the first portion 1522 and chamber 1529 of the cap 1520, respectively. Once assembled, the drug delivery system 400 may undergo a sterilization protocol to provide a sealed and sterile fluid path 440 and/or sterile needle 1516, as described above.

For example, the drug delivery system 400 may be placed within a sterilization system 900, which includes an energy source 910 and a shield 920. In various embodiments, the energy source 910 may emit x-ray, γ-ray or electrical-beam (e.g., e-beam) energy. The shield 920 may include a material with a suitable composition and/or thickness to prevent (e.g., block) energy emitted 930 from the energy source 910 from passing (e.g., penetrating) therethrough. In various embodiments, the shield 920 may comprise a material which does not emit or generate energy (e.g. x-rays, etc.) when acted upon by an energy source (or limits such emissions). For example, the shield 920 may be formed partially or entirely of aluminum having a desired thickness such as, for example, a thickness of approximately 30 mm or more.

The energy source 910 and shield 920 may be positioned relative to each other such that a portion of the energy emitted 930 from energy source 910 contacts and is blocked by the shield 920, and another portion of the energy emitted 930 is directed beyond an end of the shield 920 and remains unblocked. By way of example, the drug delivery system 400 may be positioned within the sterilization system 900 such that the entire portion of the container 1512 which contains the fluid drug is aligned with (e.g., underneath) the shield 920 and protected from the energy emitted 930 from the energy source 910. The remaining portion of the drug delivery system 400, including the distal portion 1542 of the needle 1516, the cap 1520, the fluid path 440 and cover 448, is not aligned with (e.g., extends beyond) the shield 920. Upon activation of the energy source 910, the emitted energy 930 passes through and sterilizes the entire unshielded portion of the drug delivery system 400, thereby providing a sterile and sealed fluid path. Since the energy source 910 does not generate heat, the drug delivery system 400 may remain within the sterilization system 900 as long as required for sterilization of the entire fluid path 440 without the need for any form of refrigeration, light and/or humidity control systems.

Figure 15B:
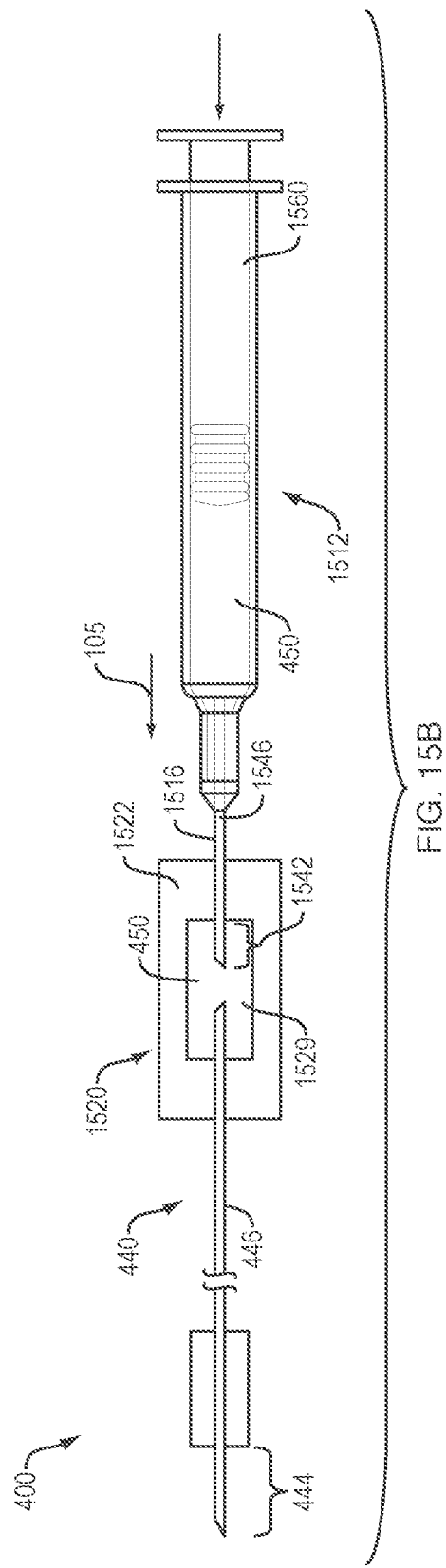
Figure 17:
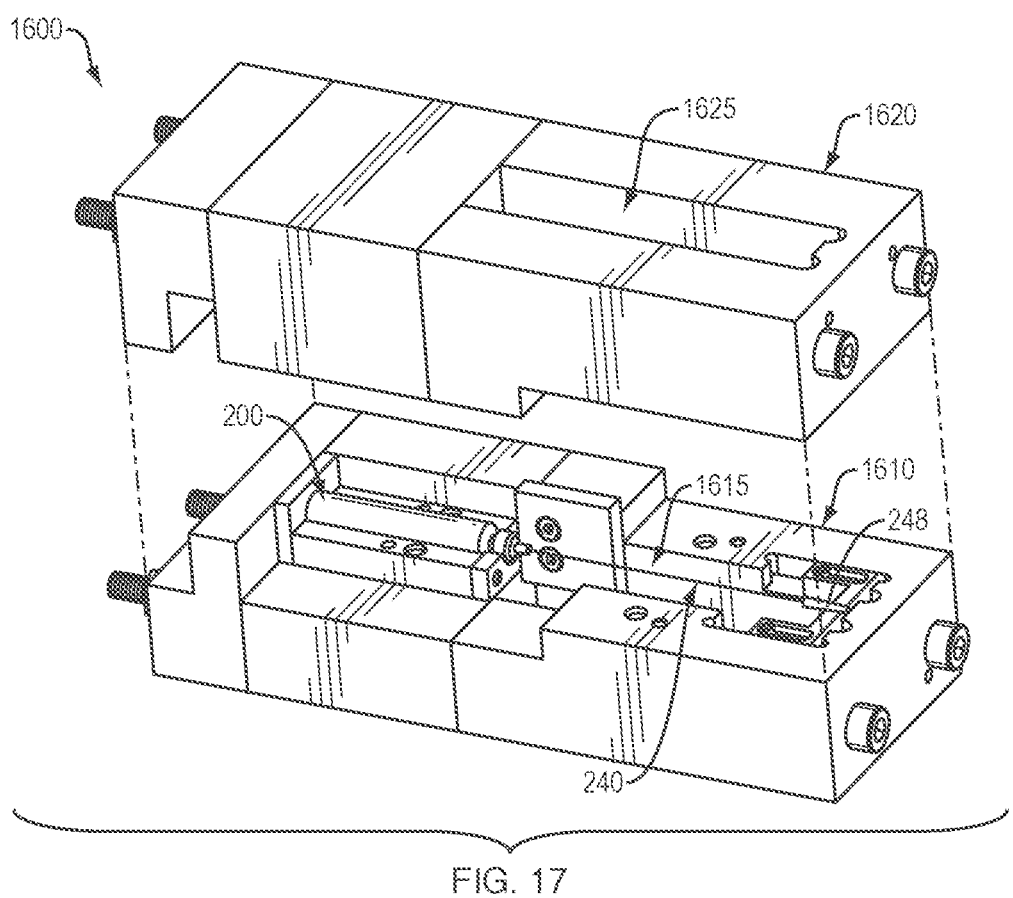
FIG. 17 provides a third schematic view of a double-barrier drug delivery system disposed within a shield assembly, according to one embodiment of the present disclosure.
Figure 18:
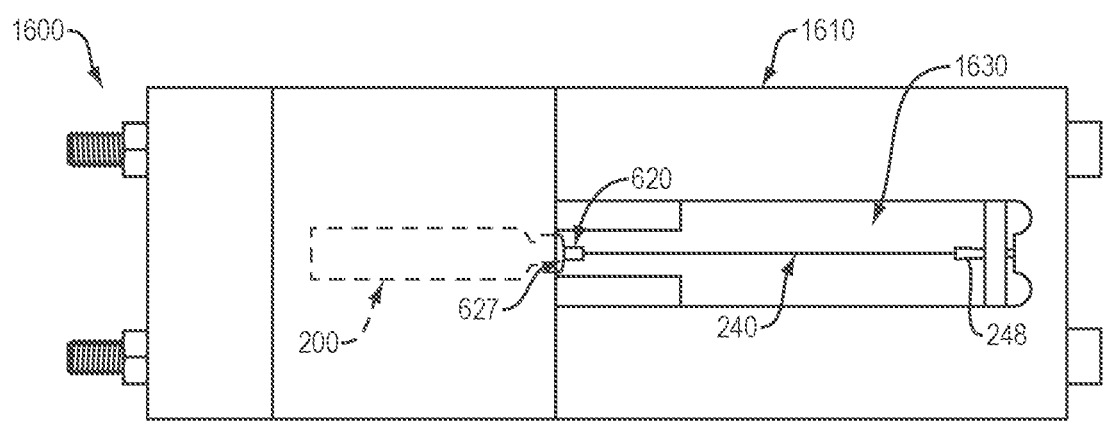
FIG. 18 provides a fourth schematic view of a double-barrier drug delivery system disposed within a shield assembly, according to one embodiment of the present disclosure.

Referring to FIG. 15B, in use and by way of example, a user may "activate" a drug delivery system 400 by distally advancing the container 1512 in the direction of the arrow 105 towards the cap 1520 such that sterile distal portion 1542 of the needle 1516 housed within the first portion 1522 of the cap 1520 enters the and chamber 1529, thereby placing the respective lumens 1546, 446 of the needle 1516 and fluid path 440 in fluid communication. The second portion 444 of the fluid path 440 may be inserted through the dermal layer, and the plunger 1560 depressed such that fluid drug 450 flows through the lumen 1546 of needle 1516 into the sterile chamber 1529 and through the sterile lumen 446 of the fluid path 440 into the patient.

In any of the embodiments of FIGS. 1-8, 11, 12 and 15A-15B, the cover 148, 248, 348, 448 may be removed from the second portion 144, 244, 344, 444 of the fluid path 140, 240, 340, 440 prior to penetrating the dermal layer of a patient. Alternatively, the second portion 144, 244, 344, 444 of the fluid path 140, 240, 340, 440 may be advanced through the cover 148, 248, 348, 448 and through the dermal layer of a patient. The drug delivery systems 100, 200, 300, 400 may include a depth setting such that only the second portion 144, 244, 344, 444 of the fluid path 140, 240, 340, 440 penetrates the dermal layer, thereby preventing a potentially non-sterile portion of the fluid path 140, 240, 340, 440 extending proximally beyond the cover 148, 248, 348, 448 from penetrating the dermal layer of the patient.

Shield Assemblies

With reference to the sterilization system 900 schematically depicted in FIG. 9 (above), in one embodiment, the shield 920 may be configured to block sterilization energy emitted from an energy source 910 along or above one side of the drug delivery system. Referring to FIGS. 16A, 16B, and 17-18, in one embodiment, the present disclosure may include a shield assembly 1600 configured to provide 360 degrees of shielding to a drug delivery system disposed therein. In various embodiments, the shield assembly 1600 may include, in combination, first and second interlocking components 1610, 1620 (interlocking component 1620 not shown in the overhead view of the assembly 1600 in FIG. 16A or the close-up view thereof in FIG. 16B). The first component 1610 may include a first window or opening 1615 extending through a width thereof, and the second component 1620 (e.g., positioned under the first component 1610) may include a corresponding second window or opening 1625 (see FIG. 17) extending through a width thereof.

Each of the first and second windows 1615, 1625 may be configured to define a contiguous opening 1630 (see FIG. 18) through the assembled shield assembly 1600, e.g., when the first and second interlocking components 1610, 1620 are locked together. One or both of the first or second components 1610, 1620 may be dimensioned to securely receive the outer surface of a portion of a drug delivery system such that the portion of the drug delivery system to be sterilized (e.g., the entire length of the fluid path 240 and portion of the cap 620 and/or septum 630) extends into the contiguous opening 1630, and the portion of the drug delivery system to be shielded from an energy source is covered, encased or otherwise blocked around an entire circumference thereof by the shield assembly 1600.

As described above, the shield assembly 1600 may be formed partially or entirely of a material (e.g., aluminum) with a sufficient thickness (e.g., approximately 30 mm or more) to prevent (e.g., shield) energy emitted from the energy source from acting upon the fluid drug and/or material components of the drug delivery system which may degrade or otherwise become compromised by such energy, and without emitting x-ray's or other deleterious energy when acted upon by the energy source (or limiting such emissions). In various embodiments, with the drug delivery system previously loaded with a fluid drug under aseptic conditions (as discussed above) and secured within an assembled shield assembly 1600, the entire shield assembly 1600 may be placed within a suitable chamber and exposed to an energy source to provide 360 degrees of sterilization of the portion of the drug delivery system extending through the contiguous opening 1630, while providing complete shielding of the remaining portion of the drug delivery system housed within the interlocked first and second components 1610, 1620.

As will be understood by those of skill in the art, the entire shield assembly 1600 with a drug delivery system disposed therein may be exposed to a given sterilization modality for a variety of times as previously determined to provide complete sterilization of the exposed portions thereof (e.g., extending through the contiguous opening 1630). In one embodiment, the energy source may rotate around the shield assembly 1600 to provide optimal exposure to the sterilization energy. Alternatively, the energy source may remain in a fixed position, and the shield assembly rotated to provide optimal exposure to the sterilization assembly. In various embodiments, one or more energy sources may be used. Further, the assembly 1600 can be exposed to a given sterilization modality in bulk—that is, multiple assemblies 1600 can be together grouped and sterilized at the same time. Any of the drug delivery devices described herein can be used with the assembly 1600.

The following examples pertain to additional embodiments:

Example 1 is a method for providing a sealed and sterile fluid path, comprising exposing a drug delivery system to an energy source, the drug delivery system comprising a container comprising a fluid drug, a cap disposed about an opening of the container, and a fluid path defining a lumen, the fluid path comprising a first portion disposed within a portion of the cap, and a second portion disposed within a cover, wherein energy emitted from the energy source passes through and sterilizes the fluid path, and does not pass through any portion of the container comprising the fluid drug.

Example 2 is an extension of example 1 or any other example disclosed herein, wherein a length of the first portion of the fluid path disposed within the cap is greater than a distance between a sharpened first end of the fluid path and an interior region of the container.

Example 3 is an extension of example 1 or any other example disclosed herein, wherein the energy emitted from the energy source is selected from the group consisting of x-ray energy, γ-ray energy and electrical-beam energy.

Example 4 is an extension of example 1 or any other example disclosed herein, wherein the cap is configured to form a fluid-tight seal about the opening of the container.

Example 5 is an extension of example 1 or any other example disclosed herein, further comprising a septum disposed between the cap and the opening of the container.

Example 6 is a method for providing a sealed and sterile fluid path, comprising exposing a drug delivery system to an energy source, the drug delivery system comprising a container comprising a fluid drug, a cap disposed about an opening of the container, a plunger slidably disposed within the container and proximal to the cap, wherein the cap and plunger are separated by an open space, and a fluid path defining a lumen, the fluid path comprising a first portion extending through the cap and disposed within the open space, and a second portion disposed within a cover, wherein energy emitted from the energy source passes through and sterilizes the fluid path, and does not pass through any portion of the container comprising the fluid drug.

Example 7 is an extension of example 6 or any other example disclosed herein, wherein a length of the first portion disposed within the open space is greater than a distance between a sharpened first end of the fluid path and an interior region of the container.

Example 8 is an extension of example 6 or any other example disclosed herein, wherein the energy emitted from the energy source is selected from the group consisting of x-ray energy, γ-ray energy and electrical-beam energy.

Example 9 is an extension of example 6 or any other example disclosed herein, wherein the cap is configured to form a fluid-tight seal about the opening of the container.

Example 10 is an extension of example 6 or any other example disclosed herein, further comprising a septum disposed within a portion of the cap.

Example 11 is a method for providing a sealed and sterile fluid path, comprising exposing a drug delivery system to an energy source, the drug delivery system comprising a container comprising a fluid drug, a cap disposed about an opening of the container, a plunger slidably disposed within the container and proximal to the cap, wherein the cap and plunger are separated by an open space, and a fluid path defining a lumen, the fluid path comprising a first portion extending through the cap and the open space and disposed within a portion of the plunger, and a second portion disposed within a cover, wherein energy emitted from the energy source passes through and sterilizes the fluid path, and does not pass through any portion of the container comprising the fluid drug.

Example 12 is an extension of example 11 or any other example disclosed herein, wherein a length of the first portion disposed within the plunger is greater than a distance between a sharpened first end of the fluid path and an interior region of the container.

Example 13 is an extension of example 11 or any other example disclosed herein, wherein the energy emitted from the energy source is selected from the group consisting of x-ray energy, γ-ray energy and electrical-beam energy.

Example 14 is an extension of example 11 or any other example disclosed herein, wherein the cap is configured to form a fluid-tight seal about the opening of the container.

Example 15 is an extension of example 11 or any other example disclosed herein, further comprising a septum disposed within a portion of the cap.

Example 16 is a sterilization system an energy source, and a drug delivery device, the drug delivery device comprising a cap having a first portion, a second portion, and a chamber disposed between the first and second portions, a container storing a fluid drug and having a needle in fluid communication with an interior region of the container, wherein a distal portion of the needle is disposed within the first portion of the cap, and a fluid path defining a lumen, the fluid path having a first portion extending though the second portion of the cap and disposed within the chamber and a second portion disposed within a cover, wherein energy emitted from the energy source passes through and sterilizes the fluid path, and does not pass through any portion of the container storing the fluid drug.

Example 17 is an extension of example 1 or any other example disclosed herein, wherein the energy emitted from the energy source is selected from the group consisting of x-ray energy, γ-ray energy and electrical-beam energy.

Example 18 is a sterilization system, comprising an energy source, the drug delivery system of claim 1, and a shield, wherein the shield is positioned between the energy source and the drug system such that energy emitted from the energy source passes through and sterilizes the fluid path, and does not pass through any portion of the container comprising the fluid drug.

Example 19 is a sterilization system, comprising an energy source, the drug delivery system of claim 6, and a shield, wherein the shield is positioned between the energy source and the drug system such that energy emitted from the energy source passes through and sterilizes the fluid path, and does not pass through any portion of the container comprising the fluid drug.

Example 20 is a sterilization system, comprising an energy source, the drug delivery system of claim 11, and a shield, wherein the shield is positioned between the energy source and the drug system such that energy emitted from the energy source passes through and sterilizes the fluid path, and does not pass through any portion of the container comprising the fluid drug.

Example 21 is a sterilization system, comprising an energy source, the drug delivery system of claim 18, and a shield, wherein the shield is positioned between the energy source and the drug system such that energy emitted from the energy source passes through and sterilizes the fluid path, and does not pass through any portion of the container comprising the fluid drug.

Example 22 is a drug delivery system, comprising a container comprising a fluid drug, a cap disposed about an opening of the container, and a sealed and sterile fluid path comprising a first portion disposed within a portion of the cap and a second portion disposed within a cover.

Example 23 is an extension of example 22 or any other example disclosed herein, wherein the cap is configured to form a fluid-tight seal about the opening of the container.

Example 24 is an extension of example 2 or any other example disclosed herein, further comprising a septum disposed between the cap and the opening of the container.

Example 25 is an extension of example 22 or any other example disclosed herein, wherein a length of the first portion of the fluid path disposed within the cap is greater than a distance between a sharpened first end of the fluid path and an interior region of the container.

Example 26 is an extension of example 22 or any other example disclosed herein, wherein the cap includes a first portion, a second portion and a third portion.

Example 27 is an extension of example 26 or any other example disclosed herein, wherein the first portion of the cap extends at least partially into a neck of the container, the second portion overlaps the opening of the container, and the third portion extends distally beyond the second portion.

Example 28 is an extension of example 26 or any other example disclosed herein, wherein the first portion of the fluid path is disposed within the third portion of the cap.

Example 29 is an extension of example 28 or any other example disclosed herein, wherein the third portion of the cap includes a chamber, and wherein the first portion of the fluid path is at least partially disposed within the chamber.

Example 30 is an extension of example 29 or any other example disclosed herein, wherein the chamber is configured to collapse as the first portion of the fluid path is proximally advanced an interior region of the container.

Example 31 is a drug delivery system, comprising a container comprising a fluid drug, a cap disposed within an end portion of the container, a plunger slidably disposed within the container and proximal to the cap, wherein the cap and plunger are separated by an open space, and a sealed and sterile fluid path, the sealed and sterile fluid path comprising a first portion extending through the cap and disposed within the open space, and a second portion disposed within a cover.

Example 32 is an extension of example 31 or any other example disclosed herein, wherein the cap is configured to form a fluid-tight seal about the opening of the container.

Example 33 is an extension of example 31 or any other example disclosed herein, wherein the plunger is configured to form a fluid-tight seal between the open space and the fluid within the container.

Example 34 is an extension of example 31 or any other example disclosed herein, wherein a length of the first portion of the fluid path disposed within the open space is greater than a distance between a sharpened first end of the fluid path and the fluid within the container.

Example 35 is a drug delivery system, comprising a container comprising a fluid drug, a cap disposed within an end portion of the container, a plunger slidably disposed within the container and proximal to the cap, wherein the cap and plunger are separated by an open space, and a sealed and sterile fluid path, the sealed and sterile fluid path comprising a first portion extending through the cap and open space and disposed within a portion of the plunger, and a second portion disposed within a cover.

Example 36 is an extension of example 35 or any other example disclosed herein, wherein the cap is configured to form a fluid-tight seal about the opening of the container.

Example 37 is an extension of example 6 or any other example disclosed herein 35, wherein the plunger is configured to form a fluid-tight seal between the open space and the fluid within the container.

Example 38 is an extension of example 35 or any other example disclosed herein, wherein a length of the first portion of the fluid path disposed within the plunger is greater than a distance between a sharpened first end of the fluid path and the fluid within the container.

Example 39 is a drug delivery system, comprising a cap, comprising a first portion, a second portion, and a chamber disposed between the first and second portions, a container comprising a fluid drug and a needle in fluid communication with an interior region of the container, wherein a distal portion of the needle is disposed within the first portion of the cap, and a sealed and sterile fluid path, the sealed and sterile fluid path comprising a first portion extending though the second portion of the cap and disposed within the chamber, and a second portion disposed within a cover.

The following examples pertain to additional further embodiments:

Example 1 is a system comprising a container having a main body and a neck, the container configured to hold a liquid drug, a cap coupled to the neck, the cap configured to seal an open end of the container, a fluid path having a first end disposed within the cap and a second end disposed within a cover, an energy source configured to emit energy, and a shield positioned adjacent to the container, the shield configured to expose the fluid path to the emitted energy while blocking exposure of the liquid drug to a substantial portion of the emitted energy.

Example 2 is an extension of example 1 or any other example disclosed herein, wherein the emitted energy is configured to sterilize the fluid path.

Example 3 is an extension of example 2 or any other example disclosed herein, wherein the emitted energy comprises an electron beam.

Example 4 is an extension of example 3 or any other example disclosed herein, wherein the shield comprises aluminum.

Example 5 is an extension of example 4 or any other example disclosed herein, wherein the aluminum shield has a thickness of at least 30 mm.

Example 6 is an extension of example 3 or any other example disclosed herein, wherein the fluid path comprises a lumen.

Example 7 is an extension of example 3 or any other example disclosed herein, wherein the liquid drug is sterilized prior to sterilizing the fluid path.

Example 8 is an extension of example 1 or any other example disclosed herein, wherein the first end of the fluid path comprises a first sharpened tip and the second end of the fluid path comprises a second sharpened tip.

Example 9 is an extension of example 8 or any other example disclosed herein, wherein the first sharpened tip is configured to pierce the cap and to extend through the cap to couple the first sharpened tip to the liquid drug based on an activation by a user.

Example 10 is an extension of example 9 or any other example disclosed herein, wherein the cap comprises a first portion configured to extend into a portion of the neck.

Example 11 is an extension of example 10 or any other example disclosed herein, wherein the cap comprises a second portion configured to overlap an end of the neck.

Example 12 is an extension of example 11 or any other example disclosed herein, wherein the cap comprises a third portion configured to extend away from the neck and the first portion of the cap.

Example 13 is an extension of example 12 or any other example disclosed herein, wherein the first sharpened tip is positioned within the first portion of the cap prior to the activation by the user.

Example 14 is an extension of example 12 or any other example disclosed herein, wherein the first sharpened tip is positioned within the third portion of the cap prior to the activation by the user.

Example 15 is an extension of example 14 or any other example disclosed herein, wherein the third portion comprises an open chamber.

Example 16 is an extension of example 15 or any other example disclosed herein, wherein the third portion is configured to collapse when the first sharpened tip pierces the cap upon activation by the user.

Example 17 is an extension of example 11 or any other example disclosed herein, wherein the cap is coupled to the neck by a crimp component overlapping the second portion of the cap.

Example 18 is an extension of example 9 or any other example disclosed herein, further comprising a septum positioned between the cap and the liquid drug.

Example 19 is a method comprising positioning a first end of a fluid path within a container configured to hold a liquid drug, positioning a second end of the fluid path within a cover, positioning a shield between an energy source and the container, and exposing the fluid path to energy emitted by the energy source to sterilize the fluid path while blocking exposure of the liquid drug to a substantial portion of the energy emitted by the energy source.

Example 20 is an extension of example 19 or any other example disclosed herein, wherein positioning the shield comprising positing an aluminum shield having a thickness of at least 30 mm between the container and the energy source.

Example 21 is an extension of example 19 or any other example disclosed herein, further comprising sterilizing the liquid drug prior to sterilizing the fluid path.

Example 22 is an extension of example 19 or any other example disclosed herein, further comprising piercing a cap sealing the container with the first end of the fluid path to couple the liquid drug to the fluid path upon activation by a user.

Example 22 is an extension of example 22 or any other example disclosed herein, further comprising piercing a septum sealing the container with the first end of the fluid path to couple the liquid drug to the fluid path upon activation by a user.

Example 23 is an extension of example 19 or any other example disclosed herein, further comprising piercing a plunger sealing the container with the first end of the fluid path to couple the liquid drug to the fluid path upon activation by a user.

Example 24 is an extension of example 19 or any other example disclosed herein, wherein positioning the shield between the energy source and the container comprises placing the fluid path and the container within a first shield component having an exposure window and coupling a second shield component to the first shield component.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A method, comprising:

positioning a shield between an energy source and a drug delivery system, the drug delivery system comprising a container, a fluid path, and a cover, the container holding a liquid drug, a first end of the fluid path within the container, and a second end of the fluid path within the cover;

emitting energy from the energy source;

exposing the fluid path to the energy emitted by the energy source to sterilize the fluid path; and blocking exposure of the liquid drug to a substantial portion of the energy emitted by the energy source.

2. The method of claim 1, further comprising positioning the first end of the fluid path within the container.

3. The method of claim 1, further comprising positioning the second end of the fluid path within the cover.

4. The method of claim 1, wherein positioning the shield comprises positioning an aluminum shield having a thickness of at least 30 mm between the drug delivery system and the energy source.

5. The method of claim 1, further comprising sterilizing the liquid drug prior to sterilizing the fluid path.

6. The method of claim 1, further comprising piercing a cap sealing the container with the first end of the fluid path to couple the liquid drug to the fluid path upon activation by a user.

7. The method of claim 6, further comprising piercing a septum sealing the container with the first end of the fluid path to couple the liquid drug to the fluid path upon activation by a user.

8. The method of claim 1, further comprising piercing a plunger sealing the container with the first end of the fluid path to couple the liquid drug to the fluid path upon activation by a user.

9. The method of claim 1, wherein positioning the shield comprises placing the fluid path and the container within a first shield component having an exposure window and coupling a second shield component to the first shield component.

10. The method of claim 1, wherein emitting energy comprises emitting x-ray energy from the energy source.

11. The method of claim 1, wherein emitting energy comprises emitting $\gamma$-ray energy from the energy source.

12. The method of claim 1, wherein emitting energy comprises emitting electrical-beam energy from the energy source.

* * * * *